United States Patent
Sohn et al.

(10) Patent No.: US 8,431,759 B1
(45) Date of Patent: Apr. 30, 2013

(54) HEAVY ALKYLBENZENE TRANSALKYLATION OPERATING COST REDUCTION

(71) Applicant: UOP LLC, Des Plaines, IL (US)

(72) Inventors: Stephen W. Sohn, Arlington Heights, IL (US); Mark G. Riley, Hinsdale, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/690,760

(22) Filed: Nov. 30, 2012

Related U.S. Application Data

(62) Division of application No. 12/917,851, filed on Nov. 2, 2010, now Pat. No. 8,350,110.

(51) Int. Cl.
*C07C 6/126* (2006.01)
*C07C 2/66* (2006.01)

(52) U.S. Cl.
USPC .......... 585/323; 585/455; 585/467; 585/470; 585/475

(58) Field of Classification Search .................. 585/323, 585/455, 467, 470, 475
See application file for complete search history.

(56) References Cited

U.S. PATENT DOCUMENTS 3,428,701 A * 2/1969 Ward ............................ 585/312

\* cited by examiner

*Primary Examiner* — Thuan Dinh Dang
(74) *Attorney, Agent, or Firm* — Arthur E Gooding

(57) ABSTRACT

A process for increasing the production of monoalkylbenzenes is presented. The process includes utilizing a transalkylation process to convert dialkylbenzenes to monoalkylbenzenes. The transalkylation process recycles a portion of the effluent stream from the transalkylation reactor back to the feed of the transalkylation reactor. The recycled dialkylbenzenes and a portion of the recycled benzene are converted to monoalkylbenzenes.

6 Claims, No Drawings

HEAVY ALKYLBENZENE TRANSALKYLATION OPERATING COST REDUCTION

CROSS-REFERENCE TO RELATED APPLICATION

This application is a Division of prior copending application Ser. No. 12/917,851 which was filed on Nov. 2, 2010, the contents of which are incorporated herein by reference thereto.

FIELD OF THE INVENTION

The present invention relates to the alkylation of benzene. In particular, the present invention relates to the conversion of dialkylbenzenes to monoalkylbenzenes.

BACKGROUND OF THE INVENTION

The alkylation of benzene with olefins produces a variety of alkylbenzene compounds that have various commercial uses. Examples include the alkylation of benzene with olefins having 8 to 16 carbons for the production intermediate compounds in the manufacture of detergents. The alkylbenzenes are sometimes referred to as phenylalkanes, and are produces as a commodity in amounts between 50,000 and 200,000 metric tonnes per year, at a large scale facility. The alkylation process comprises reacting benzene with an olefin in the presence of a catalyst at elevated temperatures. The catalysts can be homogeneous or heterogeneous catalysts such as hydrogen fluoride, aluminum chloride, silica alumina, or zeolitic catalysts.

The desired alkylated compounds are monoalkylated aromatic compounds. Two common reactions for producing monoalkylated aromatic compounds are alkylation of aromatic compounds such as benzene, and transalkylation of polyalkylated aromatic compounds. Monoalkylated aromatic compounds include linear alkylbenzenes (LAB), which are used to form linear alkylbenzene sulfonates (LABS), a common compound used in detergents, and which are manufactured from linear alkylbenzenes. One aspect of benzene alkylation has been the use of high benzene to olefin ratios for the production of alkylbenzene production. The transalkylation process reacts the polyalkylated aromatic compound with benzene to form a monoalkylated product. Both the alkylation and transalkylation processes involve the use of benzene in a relatively high molar ratio with respect the olefin or polyalkylated aromatic compound.

Currently, monoalkylated benzenes are desired, and polyalkylated benzenes are by-products that need to be removed or need to be recycled to try and produce more monoalkylated benzenes. The method of reducing the amount of polyalkylated benzenes is to increase the benzene to olefin ratio. The other method of reducing polyalkylated benzenes is to pass the polyalkylbenzenes through a transalkylation reactor. However, the industry is striving to reduce the benzene to olefin ratio, and the usual method is to use many small beds with decreasing ratios as the benzene and olefins pass through successive beds. The cost of producing a pure benzene stream is expensive, and the cost of separating and recycling benzene is expensive and energy intensive.

Methods of improving the recovery and usage of benzene can result in substantial savings in energy and expense.

SUMMARY OF THE INVENTION

The production of linear alkylbenzenes requires a substantial excess of benzene for the reaction to proceed, while limiting other undesirable side reactions. The excess benzene is expensive, and is balanced against the amount of by-products generated in the alkylation process. Reducing the amount of benzene increases the amount of dialkylbenzenes, or heavies, produced. The present invention provides a process for increasing the amount of alkylbenzenes, or monoalkylbenzenes. The process continuously supplies benzene and dialkylbenzenes to a transalkylation reactor. The reactor is operated under reaction conditions, and the benzene and dialkylbenzene react in the presence of a catalyst to generate an effluent stream comprising benzene, dialkylbenzene and monoalkylbenzene. A portion of the effluent stream is taken as a recycle stream, without separation, and passed back to the transalkylation reactor.

In one embodiment, the recycle stream comprises more than 50% of the effluent stream. Additional objects, embodiments and details of this invention can be obtained from the following detailed description of the invention.

DETAILED DESCRIPTION OF THE INVENTION

To be commercially acceptable, alkylbenzenes must meet stringent product specifications. One commercial product purpose is the use for detergent manufacture, where the alkylbenzenes are sulfonated to form surfactants. To be good detergents, the alkylbenzene must be capable of providing a sulfonated product of suitable clarity, biodegradability and efficacy. The alkylbenzenes that biodegrade the most rapidly are linear alkylbenzenes, and LAB are the object of this invention, though modified linear alkylbenzenes are also contemplated. The product should be relatively free from benzenes, e.g., less than about 1 part per million by weight (ppmw), and often less than about 0.5 ppmw. Also, the products are relatively free, e.g., less than about 50, preferably less than about 5, ppmw, from byproducts such as dialkylbenzenes, oligomers of olefins, and the like (herein referred to as "heavies"). The catalysts for the production of alkylbenzenes are not selective and other reactions of olefins can occur to produce heavies, i.e., dimers and dialkylaryl compounds. Accordingly, typical processes use a large excess of benzene to reduce the molar ratio of the sought alkylbenzene to the olefin in the reactor. However, the amount of benzene used needs to be balanced against the cost of using large amounts of benzene. The reduction in the amount of benzene results in an increase in the production of heavies. The formation of dialkylbenzene compounds is particularly problematic as the reaction approaches complete conversion of the olefin and the concentration of the alkylbenzene has thus increased thereby increasing the likelihood that an olefin molecule will react with an alkylbenzene molecule rather than benzene. To address this problem, dialkylbenzenes are processed in a transalkylation reactor to covert the dialkylbenzenes to monoalkylbenzenes and increase the monoalkylbenzene yields.

Transalkylation also uses benzene where the dialkylbenzenes are then reacted in the presence of benzene and a transalkylation catalyst to produce monoalkylbenzenes.

The present invention is a process for the production of monoalkylbenzenes. The process includes continuously supplying benzene to a transalkylation reactor, and continuously supplying heavy alkylbenzenes to the transalkylation reactor. The benzene and heavy alkylbenzenes are reacted in the presence of a transalkylation catalyst at reaction conditions to generate an effluent stream comprising benzene, heavy alkylbenzenes and monoalkylbenzenes. The process further includes recycling a portion of the effluent stream to the transalkylation reactor, without separation of the effluent stream into separate components.

It has been assumed that the monoalkylbenzene needed to be separated and recovered before recycling the benzene and heavies back to the transalkylation reactor. It was unexpectedly found that the presence of monoalkylbenzenes had no effect on the continued reaction of heavy alkylbenzenes and benzene. Without being bound by any theory, it is believed that the monoalkylbenzene is either relatively inert with respect to the transalkylation process, or that the monoalkylbenzene reacts with benzene and that this reaction has no net effect on the production of monoalkylbenzenes, i.e. the monoalkylbenzene reacting with benzene will return benzene and a monoalkylbenzene.

The effluent stream from the transalkylation reactor is split, and at least 50% of the effluent stream is recycled. In one embodiment, at least 75% of the effluent stream is recycled to the reactor. The reactor is sized and the recycle is of a sufficient amount to convert more than 50% of the heavy alkylbenzene to monoalkylbenzene. The majority of the heavy alkylbenzenes are dialkylbenzenes. The remainder of the effluent stream is passed to a monoalkylation recovery unit.

The monoalkylation recovery comprises passing the effluent stream to a benzene column, where benzene is separated from the alkylbenzenes. The benzene column creates an overhead stream comprising benzene, and a bottoms stream comprising alkylbenzenes. The bottoms stream is passed to an alkylate column, and the monoalkylbenzene is separated and passed out in an overhead stream, while the bottoms stream comprises heavy alkylbenzenes. The overhead from the benzene column, and the bottoms stream from the alkylate column can be recycled to the transalkylation reactor for further conversion of the heavy alkylbenzenes to monoalkylbenzenes.

The current practice with transalkylation is to use a high benzene to heavy alkylbenzene molar ratio. This ratio is usually 60 or greater. The present invention allows for a much lower ratio, and utilizes a molar ratio of 20:1 benzene to heavy alkylbenzene in the fresh feed. Preferably the molar ratio can be reduced to 15:1, and more preferably the molar ratio can be reduced to 10:1. The recycling of the effluent stream to the transalkylation reactor provides sufficient benzene to continue the transalkylation reactions. This process lowers the benzene to fresh feed ratio and reduces the benzene demands by the transalkylation reactor.

The process further includes a mass ratio of the recycle stream to the total effluent stream between 0.1 and 1.0, or that the recycle stream is a portion of the effluent stream between 10% and 100% of the effluent stream. A preferred recycle stream as a portion of the effluent stream is between 50% and 90% of the effluent stream. While the upper limit of the recycle stream is listed as 100%, a practical limit is 99%, and is determined by the conversion of dialkylbenzene to monoalkylbenzene. An additional constraint on the recycle is the size of the reactor. With too large a recycle, the reactor would become very large and therefore expensive. Therefore, an additional factor is balancing the cost of fresh benzene against the cost of increasing the reactor size. The benzene in the recycle stream allows for a reduction in the fresh benzene added to the feed of the transalkylation reactor. As the recycle portion of the effluent increases, the fresh benzene can be reduced until there is a balance between the benzene consumed in the reaction plus the benzene removed in the portion of the effluent stream that is not recycled with the benzene needed to replace the consumed and lost benzene.

Transalkylation reaction conditions include operating at a temperature from about 130° C. to about 270° C., preferably from about 180° C. to 240° C. At higher temperatures, a greater amount of cracking occurs with increased co-production of lights. Also higher temperatures tend to result in a loss of linearity of the alkyl group. Therefore, a more preferred transalkylation temperatures is from about 190° C. to 220° C. The transalkylation process is carried out with the reactants in the liquid phase, and therefore, moderately elevated pressures broadly ranging from about 100 kPa to 10 MPa absolute are also used for transalkylation such that the reactants remain in the liquid phase. The transalkylation reaction can be carried out as a continuous or semicontinuous process.

The transalkylation conditions including catalyst can vary widely, but are different from alkylation catalysts. Typical catalysts include those having acidic functionality. Acidic catalysts comprise zeolites having a zeolite structure type selected from the group consisting of FAU, BEA, MOR, MTW, and NES. Such zeolites include mordenite, ZSM-4, ZSM-12, ZSM-20, ZSM-38, MCM-22, MCM-36, MCM-49, UZM-8 offretite, gmelinite, zeolite Y, NU-87, and gottardite. Another class of acidic, solid catalyst components are acidified refractory oxides such as chlorided, fluorided, or sulfated alumina, gallia, boria, molybdia, ytterbia, titania, chromia, silica, zirconia, and the like and combinations thereof. Clays such as beidellite clays, hectorite clays, laponite clays, montmorillonite clays, nontonite clays, saponite clays, bentonite clays and mixtures thereof and amorphous catalysts may also find utility.

If desired, the transalkylation catalyst may be metal stabilized. The metal component typically is a noble metal or base metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Preferably the metal component comprises rhenium. Suitable metal amounts in the transalkylation catalyst range from about 0.01 to about 10 mass-percent, with the range from about 0.1 to about 3 mass-percent being preferred, and the range from about 0.1 to about 1 mass-percent being highly preferred. In some instances, it may be desirable to modify the catalyst such as by sulfiding either in-situ or ex-situ.

The catalyst may also contain a suitable binder or matrix material such as inorganic oxides. Suitable binders or matrix materials are known to those skilled in the art, and include, but are not limited to, include inorganic oxides such as one or more of alumina, magnesia, zirconia, chromia, titania, boria and silica. The relative proportion of molecular sieve or other catalytically active component in the catalyst may range from about 10 to about 99 mass-percent, with about 20 to about 90 mass-percent being preferred. A refractory binder or matrix can be used to facilitate fabrication of the catalyst, provide strength and reduce fabrication costs. The binder should be uniform in composition and relatively refractory to the conditions used in the process. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; which components can be added to the composite at any suitable point.

The present invention can be integrated into a system for the production of linear alkylbenzenes from benzene and olefins. The process comprises continuously supplying benzene and a mixture of olefins, wherein the olefins are a mixture of linear olefins having 8 to 16 carbons, to an alkylation zone. The alkylation zone is operated at alkylation conditions in the presence of an alkylation catalyst, and generates an effluent stream having benzene, linear monoalkylbenzenes and heavy alkylbenzenes. The effluent stream is separated in a separation unit and generates a first stream comprising benzene, a second stream comprising linear monoalkylbenzenes and a third stream comprising heavy alkylbenzenes. The benzene and the third stream are continuously passed to a transalkylation zone. The transalkylation zone is operated at transalkylation conditions in the presence of a transalkylation catalyst, and generates a transalkylation effluent stream having benzene, monoalkylbenzenes and heavy alkylbenzenes. The process includes passing a portion of the transalkylation effluent stream as a recycle stream back to the transalkylation zone, without separating the effluent stream.

In another embodiment, a portion, or all, of the first stream comprising benzene is passed back to the alkylation zone. In another embodiment, the first stream can be passed, either partly or entirely, to the transalkylation zone. The choice of splitting the benzene from the first stream will depend on the conditions and the amount of benzene needed to be recycled in each reaction zone.

The portion of the transalkylation effluent stream that is passed back as a recycle stream to the transalkylation zone is at least 50% of the transalkylation effluent stream. In another embodiment, the recycle stream is more than 75% of the transalkylation effluent stream.

The process comprises passing a recycle stream and a combined benzene and heavy alkylbenzene stream to the transalkylation zone. The fresh benzene and heavy alkylbenzene is fed in a molar ratio less than 20:1. The process further includes the recycle stream as a portion of the effluent stream between 10% and 100% of the effluent stream. A preferred recycle stream as a portion of the effluent stream is between 50% and 90% of the effluent stream. The recycle portion of the effluent provides benzene for the transalkylation process, and the fresh benzene can be reduced to replace the benzene consumed in the reaction plus the benzene removed in the portion of the effluent stream that is not recycled.

Alkylation conditions generally include a temperature in the range between about 80° C. and about 200° C., most usually at a temperature not exceeding about 175° C. Since the alkylation is typically conducted in at least partial liquid phase, and preferably in either an all-liquid phase or at supercritical conditions, pressures must be sufficient to maintain benzene as a liquid. The requisite pressure necessarily depends upon the temperature, but normally is in the range of about 1300 to 7000 kPa, and most usually between about 2000 and 3500 kPa. Preferably the alkylation conditions are chosen to limit substantial skeletal isomerization of the olefin.

Solid alkylation catalysts are prone to generate more heavies. Hence, for these solid catalysts the mole ratio of benzene to olefin is typically greater than 15:1. For making alkylbenzenes with reduced skeletal isomerization, the benzene to olefin ratio is often in excess of 20:1 and sometimes as much as 30:1. Alkylation catalysts comprise zeolites having a zeolite structure type selected from the group consisting of FAU, BEA, MOR, MTW, and NES. Such zeolites include mordenite, ZSM-4, ZSM-12, ZSM-20, ZSM-38, MCM-22, MCM-36, MCM-49, UZM-8, offretite, gmelinite, zeolite Y, NU-87, and gottardite. Another class of acidic, solid catalyst components are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. No. 5,196,574; U.S. Pat. No. 6,315,964 and U.S. Pat. No. 6,617,481. The catalyst may contain suitable binder or matrix material such as inorganic oxides and other suitable materials known to those skilled in the art.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A continuous process for the production of linear alkylbenzenes, comprising
    continuously supplying benzene and a mixture of linear olefin to an alkylation zone at alkylation conditions in the presence of a catalyst, wherein the linear olefins have between 8 and 16 carbon atoms, thereby generating an alkylation effluent stream comprising benzene, linear monoalkylbenzenes and heavy alkylbenzenes;
    separating the effluent stream in to a first stream comprising benzene, a second stream comprising linear monoalkylbenzenes and a third stream comprising heavy alkylbenzenes;
    continuously supplying benzene and the third stream to a transalkylation zone at transalkylation conditions in the presence of a catalyst, thereby creating a transalkylation effluent stream comprising benzene, heavy alkylbenzenes and monoalkylbenzenes; and
    passing a portion of the transalkylation effluent stream as a recycle stream back to the transalkylation zone, without separation of the components in the effluent stream; wherein the portion of the effluent stream passed back to the transalkylation reactor is more than 50% of the effluent stream and the conversion of heavy alkylbenzene is more than 50%.

2. The process of claim 1 wherein the first stream comprising benzene is returned to the alkylation zone.

3. The process of claim 1 wherein the first stream comprising benzene is passed to the transalkylation zone.

4. The process of claim 1 wherein the portion of the transalkylation effluent stream passed back to the transalkylation zone is more than 75% of the effluent stream.

5. The process of claim 1 wherein the portion of the effluent stream that is the recycle stream is between 50% and 90% of the effluent stream.

6. The process of claim 1 wherein the benzene to heavy alkylbenzenes in the feed is in a molar ratio less than 20:1.

* * * * *